United States Patent [19]

Peilloud

[11] Patent Number: 4,919,660
[45] Date of Patent: Apr. 24, 1990

[54] PROSTHETIC KNEE JOINT WITH ROLLER BEARINGS

[75] Inventor: Fernand Peilloud, Alby-Cheran, France

[73] Assignee: S. N. R. Roulementsi, France

[21] Appl. No.: 106,862

[22] Filed: Oct. 13, 1987

[30] Foreign Application Priority Data

Oct. 14, 1986 [FR] France ................... 86 14251

[51] Int. Cl.$^5$ ..................... A61F 2/38; A61F 2/30
[52] U.S. Cl. ........................ 623/20; 623/18; 403/158; 403/162
[58] Field of Search .............. 623/18, 20, 39, 22, 623/23, 21; 403/158, 162, 163

[56]     References Cited
U.S. PATENT DOCUMENTS

| 1,124,220 | 1/1915 | Gaines et al. | 623/39 |
| 1,690,194 | 11/1928 | Girton | 623/39 |
| 2,055,066 | 9/1936 | Buchstein | 623/39 X |
| 2,277,548 | 3/1942 | Jackson | 623/39 |
| 2,822,550 | 2/1958 | Grodzki | 623/39 |
| 3,723,995 | 4/1973 | Baumann | 623/22 |
| 3,772,709 | 11/1973 | Swanson | 623/18 X |
| 3,996,624 | 12/1976 | Noiles | 623/20 |
| 4,136,405 | 1/1979 | Pastrick et al. | 623/20 |
| 4,243,341 | 1/1981 | Kabay et al. | 403/158 X |
| 4,507,005 | 3/1985 | Siewert et al. | 403/162 X |
| 4,652,167 | 3/1987 | Garman | 403/158 |
| 4,655,778 | 4/1987 | Koeneman | 623/18 X |

FOREIGN PATENT DOCUMENTS

| 2024583 | 11/1970 | Fed. Rep. of Germany | 623/22 |
| 2114287 | 9/1972 | Fed. Rep. of Germany | . |
| 1532997 | 7/1968 | France | . |
| 366386 | 2/1932 | United Kingdom | 403/158 |
| 1328497 | 8/1973 | United Kingdom | . |

OTHER PUBLICATIONS

Fundamentals of Machine Component Design, Robert Juvinall, pp. 427, 429–433, 1983.
Metal Progress Material & Processing, Databook 1981, vol. 120, No. 1, Jun. 1981, pp. 90–91, American Society for Metal; "Cobalt-Base Alloys", Elgiloy et MP35N.

Primary Examiner—Richard J. Apley
Assistant Examiner—David J. Bender

[57]     ABSTRACT

Knee joint prosthesis of the type including a first and second element (1, 2) capable of being secured rigidly to the bones connected by the joint. The first element (1) carries a clevis (3) through which the axis XX' of a bending pivot (4) passes. The second element (2) carries an eye (5) introduced between the legs of the clevis (3). The pivot (4) includes a pin (41) carrying on the outside a bearing ring (43) fitted in the eye (5) of the joint and lateral stops (44, 44') with a diameter corresponding to that of the ring (43), respectively fitted in the clevis (3).

12 Claims, 2 Drawing Sheets

PROSTHETIC KNEE JOINT WITH ROLLER BEARINGS

FIELD OF THE INVENTION

The invention relates to a knee joint prosthesis of the type comprising a first and a second element capable of being secured rigidly to the respective bones connected by the knee joint. The first element carries a clevis through which the axis of a bending pivot passes, and the second element carries an eye introduced between the legs of the clevis.

BACKGROUND OF THE INVENTION

Publication FR-A-2 330 375 describes such a prothesis studied so as to be installed surgically by pins in the medullary canals of the femur and tibia.

A problem posed by this type of prosthesis resides in the fact that the compression loads tend to wear quickly the constituents of the joint or to produce particles and metallic dust (from one or more metal elements of the joint) which become the cause of complications and infections.

When the hinge pin of the prosthesis is immobilized in rotation and in translation with respect to the clevis, the relative movements between the elements of the prosthesis consist of slidings in rotation between the plane or cylindrical surfaces in contact. The friction forces thus brought into play are considerable and proportional to the weight of the user of the prosthesis, and they quickly lead to a wear of the joint and to a loss in its precision of operation. A partial remedy to this drawback resides in the use of polymer friction bearings because they reduce the risk of complications of an infectious nature. However, their low resistances to wear and to creep quickly lead to a loss of the precision of adjustment and operation of the prosthesis.

OBJECTS OF THE INVENTION

The invention has as its object a joint prosthesis which applies a bending pivot to rolling elements the components of which exhibit a yield strength essential to the good operation of the prosthesis, in its zones in mutual contact subjected to Hertz pressures.

Another object of the invention is a preassembled hinge pin that can be quickly incorporated into an existing prosthesis, to avoid repeating the entire surgical process of positioning the prosthesis or lesions of the ligaments necessary for damping the forces and offering an additional guiding for the joint.

Another object of the invention is to create a knee joint prosthesis that is simple to produce and to assemble which makes possible, with satisfactory precision, the various functional movements of the joint.

SUMMARY OF THE INVENTION

According to the invention, the bending pivot consists of a central pin carrying on the outside a bearing ring fitted in the eye of the joint and lateral stops with a diameter corresponding to that of the ring, respectively fitted in the clevis.

BRIEF DESCRIPTION OF THE DRAWINGS

A preferred embodiment of the invention is more completely described below with reference to the accompanying diagrammatic drawings in which.

DETAILED DESCRIPTION OF THE PRESENTLY PREFERRED EMBODIMENT

Figure 1:
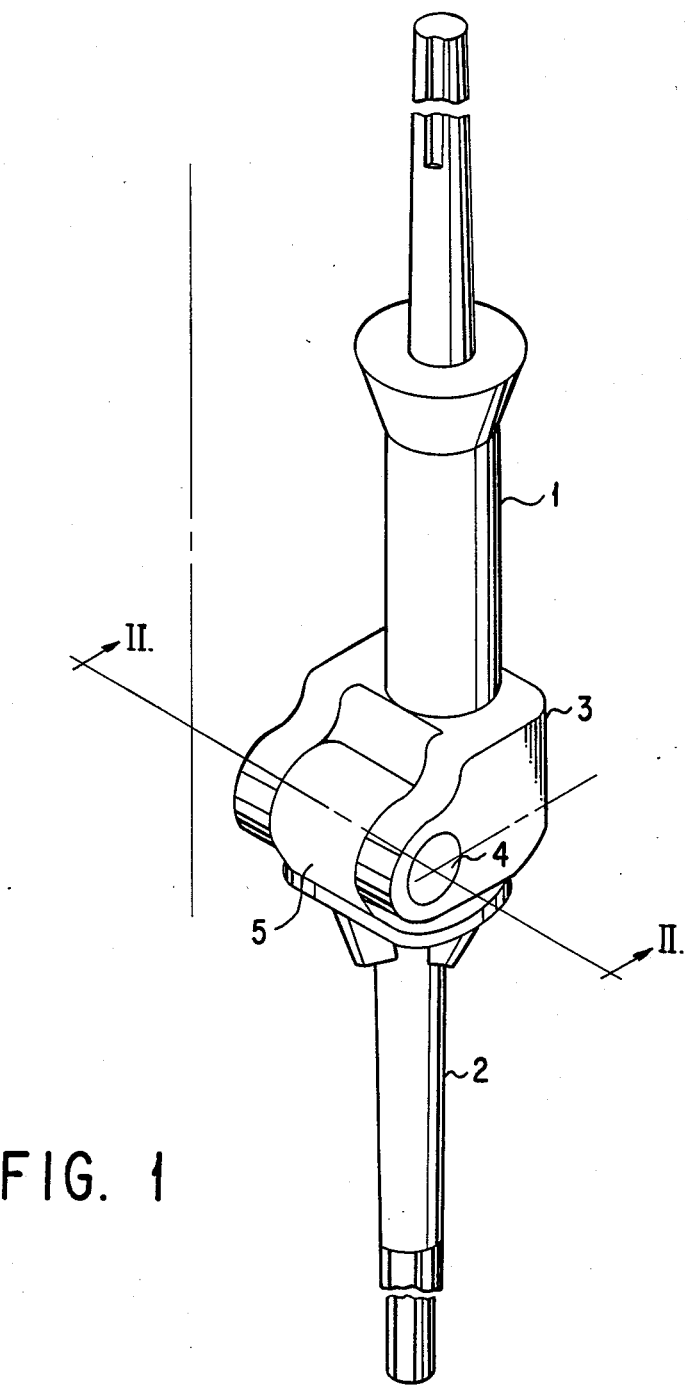
FIG. 1 is a view in perspective of the knee joint prosthesis in elongated position.

The implantable knee joint prosthesis described below is composed of an element 1 in the form of a pin intended to be fastened in the medullary canal of the tibia and an element 2 in the form of a pin intended to be fastened in the medullary canal of the femur.

The element 1 carries a clevis 3 through which axis XX' of a bending pivot 4 passes.

The element 2 carries an eye 5 introduced between the legs of the clevis 3 and through which the same axis XX' of the bending pivot 4 passes.

Figure 2:
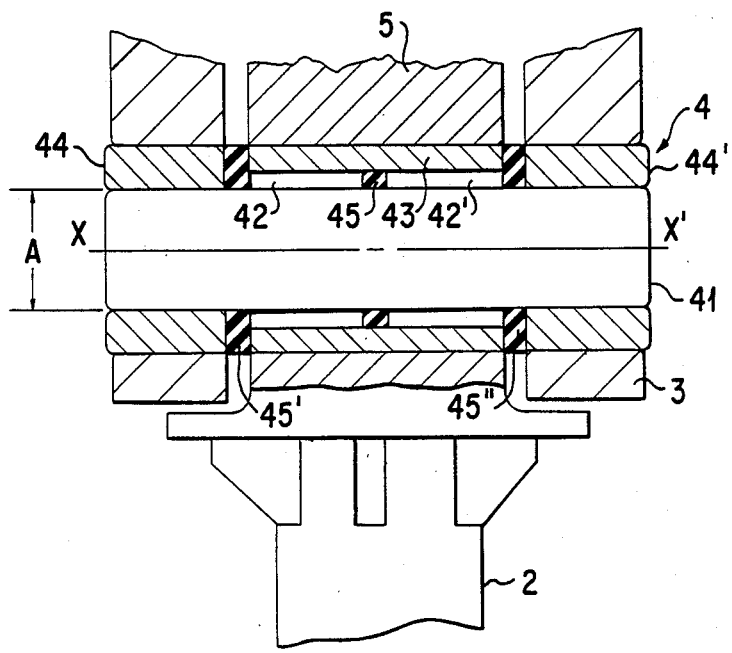
FIG. 2 is a view in partial section of the joint along line 11—11 of FIG. 1.
Figure 3:
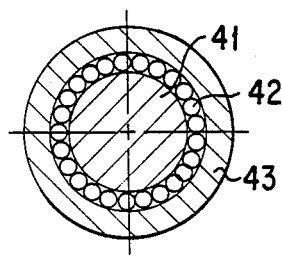
FIG. 3 is a cross-section of the bearing and pin.

As is shown in FIG. 2, the bending pivot 4 consists of a solid pin 41 of diameter A on which two sets of rolling bodies 42, 42' roll without sliding. The rolling bodies 42, 42' may consist, by way of example, of cylindrical needles separated by a polyethylene washer 45. The rolling bodies 42, 42' and the polyethylene washer 45 are surrounded by a ring 43 fitted in the eye 5 of the joint.

It should be noted that the geometry of the rolling bodies 42, 42' is not limited to the single example described. They could just as well be to balls, cylindrical or conical rollers, or combinations of these bodies.

The ring 43 is placed between two lateral stops 44, 44' of the same diameter as that of the ring 43, fastened solidly to the ends of the solid pin 41 and fitted in the clevis 3. The function of the lateral stops 44, 44' is to assure the guiding and axial immobilization of the ring 43 in relation to the solid pin 41.

Two polyethylene separation washers 45', 45" are mounted with play on the solid pin 41. The polyethylene separation washers 45', 45" preferably possess a diameter slightly less than the diameter of the ring 43. The polyethylene separation washers 45', 45", are placed between the respective lateral faces of the ring 43 and each of the lateral stops 44, 44' to facilitate a gentle friction during the angular movements between the ring 43 and the lateral stops 44, 44'.

In the embodiment shown, the lateral stops 44, 44' are rigidly mounted on the solid pin 41 by mechanical contact between the bore of the lateral stops 44, 44' and the surface of the solid pin 41. However, any other fastening means can be envisaged. The lateral stops 44, 44' protect the bearing from the stresses applied during the surgical process of mounting the prosthesis.

The materials used for the production of the principal constituents of the pivot (such as the solid pin 41, the rolling bodies 42, 42', the ring 43, and the lateral stops 44, 44') are alloys resistant to the corrosion of the human biological environment without reactions with the other materials that make up the prosthesis. Preferably, a cobalt-chromium-molybdenum-nickel alloy will be used. Moreover, the solid pin 41, the rolling bodies 42, 42', and the ring 43 are specially treated to obtain a sufficient mechanical strength for the mounting and assembly operations and for the contact pressures due to the forces applied to the prosthesis during its operation.

By way of information, hardness $H_{RC}$ of the alloy determined by Rockwell test using a tapered diamond brale will be greater than the number 50 and its yield strength will be greater than 1800 MPa.

By way of examples, either one or the other of the alloys according to A or to B defined below can be used:

| ALLOY A | | ALLOY B | |
| --- | --- | --- | --- |
| Cobalt | 29.5 to 39% | Cobalt | 31 to 50% |
| Nickel | 33 to 37% | Nickel | 15 to 18% |
| Chromium | 19 to 21% | Chromium | 18.5 to 21.5% |
| Molybdenum | 9 to 10.5% | Molybdenum | 6.5 to 7.5% |
| Iron | max 1% | Iron | 9 to 20% |
| Titanium | max 1% | Beryllium | max 0.001% |
| Carbon | max 0.025% | Carbon | max 0.15% |
| Manganese | max 0.15% | Manganese | 1 to 2% |
| Silicon | max 0.15% | | |
| Phosphorous | max 0.015% | | |
| Sulfur | max 0.010% | | |

These alloys are cold-hammered then treated thermally to impart to them the desired yield strength.

The pivot pin is immobilized axially in the clevis 3 or in the eye 5 (for example, by means of a bolt carried, as desired, by the clevis 3) and immobilizing any one of the lateral stops 44, 44' or by eye 5 and immobilizing the ring 43. Nevertheless, it will be noted that other immobilization processes can be envisaged (such as gluing or crimping) without thereby going outside the scope of the invention.

I claim:

1. A prosthetic knee joint comprising:
   (a) a first element sized and shaped to be fastened in the medullary canal of tibia;
   (b) a second element sized and shaped to be fastened in the medullary canal of a femur;
   (c) a clevis having two spaced legs carried by one of said first and second elements;
   (d) an eye carried by the other one of said first and second elements and received by the two spaced legs of said clevis; and
   (e) a pivot shaft projecting through said eye and received in the two spaced legs of said clevis, said pivot shaft comprising:
      (i) a ring mounted in said eye;
      (ii) at least one rolling body mounted in said ring;
      (iii) a lateral stop received in a bore in each one of the two spaced legs of said clevis;
      (iv) a pin received in said at least one rolling body so as to roll without sliding therein and in each one of said lateral stops; and
      (v) two separation washers mounted on said pin, one of said two separation washers being located between and in axial engagement with each end of said ring and the adjacent one of said lateral stops.

2. A prosthetic knee joint as recited in claim 1 wherein:
   (a) two rolling bodies are received in said ring and
   (b) said two rolling bodies are separated by a washer.

3. A prosthetic knee joint as recited in claim 2 wherein said washer is made of polyethylene.

4. A prosthetic knee joint as recited in claim 1 wherein said at least one rolling body comprises a plurality of cylindrical needles.

5. A prosthetic knee joint as recited in claim 1 wherein said lateral stops have the same diameter as said ring.

6. A prosthetic knee joint as recited in claim 1 wherein said lateral stops are fastened solidly to said pin.

7. A prosthetic knee joint as recited in claim 1 wherein said two separation washers are made of polyethylene.

8. A prosthetic knee joint as recited in claim 1 wherein said two separation washers possess a diameter slightly less than the diameter of said ring.

9. A prosthetic knee joint as recited in claim 1 wherein said pin is solid.

10. A prosthetic knee joint as recited in claim 1 wherein said pin, said rolling bodies, said ring, and said lateral stops are made of alloys that are resistant to the corrosion of the human biological environment and that do not react with the other materials that make up said prosthetic knee joint.

11. A prosthetic knee joint as recited in claim 10 wherein said alloys are cobalt-chromium-molybdenum-nickel alloys.

12. A prosthetic knee joint as recited in claim 10 wherein said alloys have an $H_{RC}$ hardness greater than 50 and a yield strength greater than 1800 MPa.

* * * * *

UNITED STATES PATENT AND TRADEMARK OFFICE
CERTIFICATE OF CORRECTION

PATENT NO. :  4,919,660
DATED     :  APRIL 24, 1990
INVENTOR(S) :  FERNAND PEILLOUD

It is certified that error appears in the above-identified patent and that said Letters Patent is hereby corrected as shown below:

On the title page, item [73]

In line 1, of the Assignee, delete "Roulementsi" and insert --Roulements--.

Signed and Sealed this

Twenty-second Day of October, 1991

Attest:

HARRY F. MANBECK, JR.

*Attesting Officer*   Commissioner of Patents and Trademarks